United States Patent [19]

Roberts et al.

[11] 4,224,451

[45] Sep. 23, 1980

[54] PROCESS FOR THE PREPARATION OF 2-ARYL-2H-BENZOTRIAZOLES

[75] Inventors: Rex D. Roberts, Somerville; William B. Hardy, Bound Brook, both of N.J.

[73] Assignee: American Cyanamid Company, Stamford, Conn.

[21] Appl. No.: 971,621

[22] Filed: Dec. 20, 1978

[51] Int. Cl.$^2$ ............................................. C07D 249/20
[52] U.S. Cl. ..................................... 548/260; 548/259
[58] Field of Search .................... 260/308 B; 548/260, 548/259

[56] References Cited

U.S. PATENT DOCUMENTS

| 2,362,988 | 11/1944 | Conzetti et al. | 548/259 |
| 4,001,266 | 1/1977 | Rody et al. | 548/260 |

*Primary Examiner*—Paul M. Coughlan, Jr.
*Attorney, Agent, or Firm*—Bruce F. Jacobs

[57] ABSTRACT

A two stage reductive ring closure of o-nitrophenylazophenols produces 2-aryl-2H-benzotriazoles by (a) reacting an organic solvent solution of azophenol with an excess of an aqueous solution of a sulfhydrate or sulfide to form an N-oxide and (b) reducing the N-oxide with an alkali metal hydroxide plus zinc or tin.

10 Claims, No Drawings

PROCESS FOR THE PREPARATION OF 2-ARYL-2H-BENZOTRIAZOLES

This invention relates to an improved process for the preparation of 2-aryl-2H-benzotriazoles by the reductive ring closure (triazolization) of an o-nitrophenylazophenol. In particular, it relates to an improved two-stage reductive ring closure of 2-(2-nitrophenylazo)-4-(1,1,3,3-tetramethylbutyl)phenol to 2-[2-hydroxy-5-(1,1,3,3-tetramethylbutyl)-phenyl]-2H-benzotriazole.

The compounds prepared by the present invention are known UV absorber compounds for a wide range of thermoplastic polymers; see U.S. Pat. Nos. 3,004,896, 3,239,194, and 3,773,751.

The conventional method for the reductive ring closure has been to use zinc and alkali metal hydroxide as disclosed in U.S. Pat. No. 3,773,751. This method is characterized by low productivity when conducted on a commercial scale; often by unsatisfactory color and purity without recrystallization; and is accompanied by the problem of separating large quantities of zinc oxide from the reaction mixture. In addition, some cleavage of the azo bond results, leading to oxidizable impurities and some loss of yield.

U.S. Pat. No. 4,041,044 describes the reduction of two types of azophenol compounds to benzotriazoles using zinc and alkali metal hydroxide. The principle compound of the present invention is of Type 2 (see Col, 4, 1. 40-43), i.e., those in which there is no substituent (other than a hydrogen atom) ortho to the phenolic hydroxyl group:

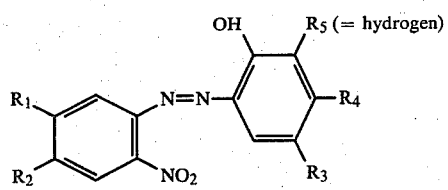

In the patented process 1.2 to 1.7 moles of alkali metal hydrooxide is used per mole of azophenol and the zinc must contain <150 ppm of iron. The reaction solvent is an aromatic hydrocarbon-water two phase system. The disclosure claims that prior art zinc/NaOH reductions gave impurities which required recrystallization since they had used large quantities of sodium hydroxide and zinc containing iron impurities. However, Example 15 of the patent shows a yield of only 62.9%.

U.S. Pat. No. 2,362,988, describes the preparation of water-soluble benzotriazoles. The patent teaches reduction using alkali sulfide/water at 80°-100° C. or zinc-/aqueous ammonia (see Col. 3, lines 33-43). The compounds of the present invention are not water-soluble. Moreover, the reduction of an azo group using alkali sulfide is known.

Chakrabarty and Dutts, J. Ind. Chem. Soc. 5, 555-559 (1928) state that reduction of 2-(2-nitrophenylazo)-4-methyl phenol:

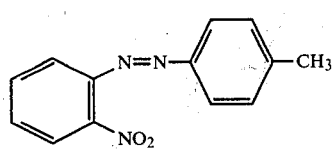

with alcoholic ammonium sulfide gives the benzotriazole 2-(4-methyl phenyl)-2H-benzotriazole:

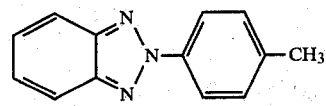

This was disputed by Ross and Warwick, J. Chem. Soc. 1956, p 1724-1732 (see p 1728) who confirmed the work of Elbs, J. prakt. Chem. 1924, p 108, who got instead the N-oxide:

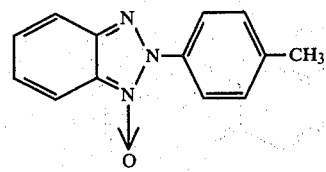

Neither of these references, therefore, teach the reductive ring closure of the o-nitrophenylazophenol to the benzotriazole.

Jancis (Uniroyal), U.S. Pat. No. 3,978,074, uses a high pressure catalytic hydrogenation in the presence of platinum sulfide/NaOh. This process produces more cleavage of the azo bond and gives products of lower purity. Moreover, the process requires high pressure equipment.

A catalytic reduction process is also described in each of:

German OLS No. 2,621,006 (filed U.S. 5/14/75, Ser. No. 577,383)

German OLS No. 2,620,896 (filed U.S. 5/14/75, Ser. No. 577,386)

Belgium Pat. No. 841,770 (filed U.S. 5/14/75, Ser. No. 577,385)

Belgium Pat. No. 841,769 (filed U.S. 5/14/75, Ser. No. 577,384)

Finally, German OLS No. 2,454,889 describes a process for reduction of the azophenols without isolation of the N-oxide intermediate using 0.5 equivalent of hydrazine in a high boiling ether solvent in the presence of base at 70°-100° C.

The prior art activity in finding better methods for the reduction of o-nitrophenyl azophenols to benzotriazoles illustrates the interest in the process in the industry, since there has not been a completely satisfactory method for the manufacture of the benzotriazoles.

The two-stage reductive ring closure of the present invention is applicable to o-nitriphenylazophenols of the formula (I)

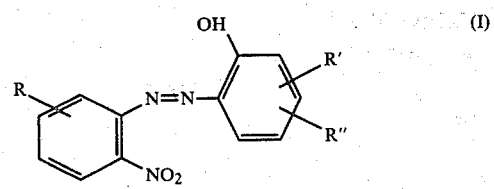

wherein R=hydrogen, alkyl (1-8 carbon atoms), alkoxy (1-8 carbon atoms) or halogen (preferably chlorine or bromine)
R'=alkyl (1-8 carbon atoms) or hydrogen
R"=alkyl (1-8 carbon atoms)

with the proviso that at least one of R' and R" has at least 4 carbon atoms, to provide 2-aryl-2H-benzotriazoles of formula (II)

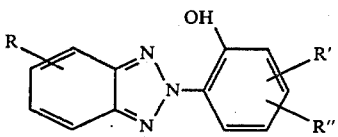

(II)

wherein R, R', and R" are as defined.

A preferred scope covers compounds (III)

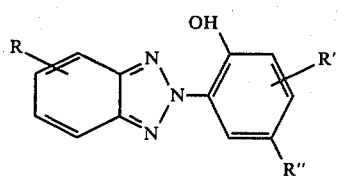

(III)

wherein R, R' = hydrogen and R" = tertiary alkyl, preferably tertiary octyl.

The reductive ring closure is conducted in two stages and proceeds via an intermediate benzotriazole N-oxide (IV) which may be isolated, if desired.

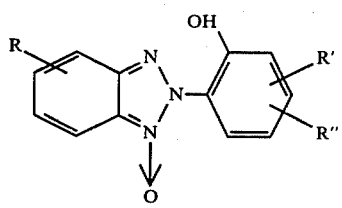

IV

Stage One is the reduction of the o-nitrophenylazophenol (I) to the corresponding N-oxide (IV) using an aqueous solution of an alkali metal or ammonium sulfhydrate or alkali metal or ammonium sulfide, preferably sodium sulfhydrate or sodium sulfide (NaSH or Na₂S) in a two-phase system of water and an aromatic hydrocarbon (benzene, toluene, xylene, etc.) or a higher aliphatic hydrocarbon (e.g. VM & P Naphtha, which is a mixture of paraffins and naphthenes; the naphthenes are essentially cyclopentane and cyclohexane derivatives), or a mixture thereof. Higher dialkyl ethers, i.e., containing more than 4 carbon atoms, may also be used.

Stage Two consists of the reduction of (IV) in the same two-phase solvent system using zinc or tin metal, preferably zinc, and alkali metal hydroxide (preferably NaOH). The reactions with the preferred catalysts are as shown below.

Stage One

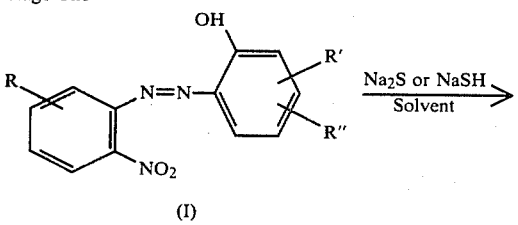

(I)

-continued

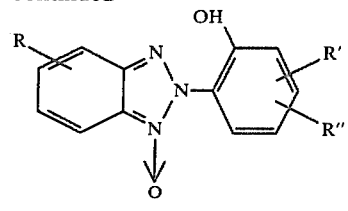

(IV)

Stage Two (IV) $\xrightarrow[\text{Solvent}]{\text{Zn/NaOH}}$

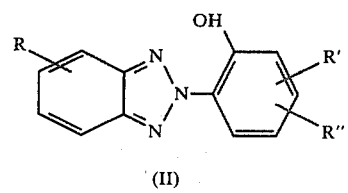

(II)

The process of the present invention increases productivity by 60–70%; gives product of good color and high purity without recrystallization; provides complete conversion in Stage 1 to the benzotriazole N-oxide, which can be isolated and stored for later use (the oxide forms but can't be isolated in the zinc reduction). Moreover, the exotherm is more readily controlled, there is virtually no azo bond cleavage, and only small amounts of zinc oxide need to be removed since much less zinc is used in Stage 2.

The o-nitro azophenol starting material may be made in a conventional manner, e.g., as described in U.S. Pat. No. 3,773,751. Following preparation of the o-nitrophenyl azophenol (I), the compound is reduced to the corresponding benzotriazole N-oxide (IV) using, in the first stage of the reduction, alkali metal, or ammonium sulfide or alkali metal or ammonium sulfhydrate, preferably sodium sulfhydrate, in a two-phase system of water and a waterimmiscible aromatic or aliphatic hydrocarbon or higher dialkyl ether solvent. The preferred solvent is toluene, although benzene, xylene and the like may also be used. Aliphatic solvents include hexane, heptane, etc., and VM & P naphtha, which is approximately 50/50 paraffins and naphthenes (primarily derivatives of cyclopentane and cyclohexane). Mixtures of aromatic and aliphatic hydrocarbon solvents may be used. The amount of solvent preferably should be the minimum amount required to dissolve both the starting materials and the product at the reaction temperatures used. The sulfide or sulfhydrate used should preferably be in excess of the amount stoichiometrically required for the reduction, preferably from about 10 to 50 percent in excess of the required amount. The reaction temperature should be a temperature above room temperature, e.g., from about 40° C. to 80° C., preferably about 50°–60° C. The rate of addition of the sulfide or sulfhydrate may vary depending on the magnitude of the excess used. The addition time may be from about 15 minutes to about 6 hours; e.g., less than about one hour if the excess is 30% and up to about 5 hours if the excess is only 10%. It is not desirable to have excess reducing agent in contact with the N-oxide for too long a time, in order to avoid the formation of impurities. Thus, the larger the excess, the shorter the addition time. Alternatively, the two-phase mixture may be added to the sulfhydrate or sulfide.

Following the sulfide reduction to the N-oxide, an emulsion is formed. This is broken by the addition of a strong electrolyte i.e., sodium chloride, sodium sulfate, calcium chloride, sodium hexametaphosphate, polymeric electrolytes, etc., preferably an aqueous solution of sodium chloride, which also removes excess sulfide from the mixture. The aqueous layer is withdrawn and the organic layer is washed with water. At this point, the N-oxide may be recovered from the organic solution by cooling or by precipitation with an alcohol. Alternatively, additional water may be added to again form a two-phase reaction mixture for stage two of the reduction. Zinc or tin is added, about 1 to 2 moles per mole of N-oxide, preferably 1.2 to 1.4 moles per mole of N-oxide. Alkali metal hydroxide, about 1.5 to 2.5 moles per mole of N-oxide, preferably about 1.7 to 2 moles, is then added over a period of time sufficient to maintain the temperature in the range of about 50°–75° C., preferably about 60° C. Addition time at 60° C. is generally about 30 minutes to one hour.

A strong inorganic acid such as hydrochloric acid may then be added to destroy the zinc or tin and to neutralize the alkali metal hydroxide. The reaction mixture is filtered, the organic phase separated and washed with water, and the product isolated by cooling or by precipitation with methanol. The yield of product is about 84–85%, based on 99% pure o-nitrophenyl azophenol and has a purity of about 99% without recrystallization.

EXAMPLE 1

To a solution of 59.4 grams of 99% pure 2-(2'-nitrophenylazo)-4-tertiary octyl phenol in 45 ml. of toluene at 60° C. was added a solution of 249 grams (34% real) sodium sulfhydrate, 11.7 grams of 50% sodium hydroxide and 15 ml. of water. The solution was added over a period of about 60 minutes. The toluene layer was separated from the aqueous layer and washed in succession with 5% and 10% solutions of sodium chloride in 50 ml. of water.

To the washed toluene solution was added 30 ml. of water and 14.2 grams of zinc dust. This was stirred as a solution of 22.5 grams of 50% sodium hydroxide was added over a period of about 30 minutes at 50°–55° C. The temperature increased to 60° C. and the reaction mixture was stirred at 60° C. for about 3 hours. Then 68 ml. of 37% hydrochloric acid was added over a period of 30 minutes. The toluene layer was separated from the aqueous layer and filtered through Hyflo filter aid. A mixture of 14 ml. of VM & P Naphtha and 150 ml. of methanol was added to the toluene solution and the mixture cooled to −5° C. The white crystalline product was filtered, washed with 250 ml. of methanol and dried. The product 2-(2'-hydroxy-5'-tert.octyl phenyl)-benzotriazole (46 grams, 85% yield) has a m.p. of 101.0°–103.2° C. Cryoscopic purity=99 mole percent.

EXAMPLE 2

Sodium sulfhydrate liquor (17.8 grams, 34% real) was added at 60° C. over a period of about 30 minutes to a mixture of 59.4 grams of 99% pure 2-(2'-nitrophenylazo-4-tertiary octylphenol, 59 ml. of VM & P Naptha, 23 ml. of toluene and 30 ml. of water. The reaction mixture was stirred for about one hour at 60° C. and the reaction mixture was washed successively with (1) 75 ml. of water and 10 grams of sodium chloride, (2) 75 ml. of water, 3 grams of 50% aqueous sodium hydroxide and 10 grams of sodium chloride in two separate portions. Then 28 ml. of water and 22.5 grams of 50% sodium hydroxide was added. Zinc dust (14.2 grams) was added in 6 portions over an hour at 50°–55° C. When all the zinc was added, the reaction mixture was stirred for 2 hours at 60° C., and then 73 ml. of concentrated hydrochloric acid was added over a period of 30–60 minutes at 60° C. The reaction mixture was allowed to settle and the aqueous layer was separated. The naphtha-toluene layer was washed with 50 ml. of water, filtered and then 150 ml. of methanol was added. On cooling to −5° C. the product crystallized. It was filtered, washed with 400 ml. of methanol and dried. A white solid, m.p. 102°–103.5° C. was obtained in 76.8% yield (41.5 grams). Mole percent cryoscopic purity was 99%.

EXAMPLE 3

A solution of 19.1 grams (60% real) sodium sulfide in 45 ml. of water was added over a period of one hour to 59.3 grams of 2-(2'-nitrophenylazo-4-tertiary octyl phenol in 45 ml. of toluene. The mixture was stirred for 2 hours at 50°–55° C. The water phase was separated and the organic phase was washed twice with 20% brine solution. Then 25 ml. of concentrated hydrochloric acid and 100 ml. of toluene was added, the mixture heated to 90° C. and the water layer again separated. The toluene layer was filtered and evaporated. The solid product was recrystallized from aqueous isopropanol to give 49.4 grams (91.6% yield based on the phenol starting material), m.p. 119.2°–121.4° C.

EXAMPLE 4

A solution of 39 grams (60% real) of sodium sulfide in 75 ml. of water was added over a period of 20 minutes to 88.7 grams of 2-(2'-nitrophenylazo)-4-tertiary octyl phenol in 67 ml. of toluene at 60° C. The reaction mixture was stirred for one hour at 55°–60° C. The water layer was separated and the organic layer washed successively with 100 ml. and 200 ml. of 20% brine solution. Then, 32.7 grams of zinc dust and 50 ml. of water was added, followed by 33.7 grams of 50% sodium hydroxide solution over a period of 30 minutes, maintaining the reaction temperature at 60°–65° C. Concentrated hydrochloric acid (230 ml.) was then added over 30 minutes at 50°–60° C. The water layer was separated and the toluene layer filtered through Hyflo filter aid. Methanol (300 ml.) was added and the mixture cooled to −5° C. The product was filtered, washed with 200 ml. of methanol and dried. There was obtained 61.1 grams (75.6%) of white solid, m.p. 103.5°–104.5° C.

EXAMPLE 5

The procedure of Example 1 is repeated while varying the starting compound and the following compounds are produced:
a. 2-[2'-hydroxy-4',5'-di(tertbutyl)phenyl]-2H-benzotriazole.
b. 2-[2'-hydroxy-3',5'-di(tertamyl)phenyl]-2H-benzothriazole
c. 2-[2'-hydroxy-4'-tertbutylphenyl ]-2H-benzotriazole.
d. 5-chloro-2-[2'-hydroxy-3'-tertbutyl-5'-methylphenyl]-2H-benzotriazole.
e. 5-chloro-2-[2'-hydroxy-3',5'-di(tertbutyl)phenyl]-2H-benzotriazole.

What is claimed is:
1. An improved process for the preparation of 2-aryl-2H-benzotriazoles of the formula (I):

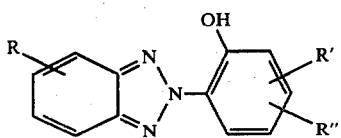

wherein R is hydrogen, alkyl having 1 to 8 carbon atoms, alkoxy having 1 to 8 carbon atoms, or halogen; R' is hydrogen or alkyl having 1 to 8 carbon atoms and R'' is alkyl having 1 to 8 carbon atoms, with the proviso that at least one of R' and R'' has at least 4 carbon atoms, by reduction, in a first stage, at a temperature of about 40° C. to 80° C., of the corresponding o-nitrophenyl azophenol of the formula (II):

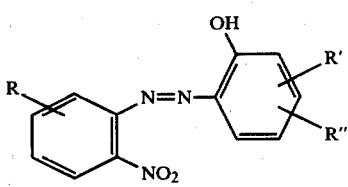

which comprises combining an aqueous solution of an alkali metal or ammonium sulfhydrate or sulfide and a two-phase mixture of water and a solution of said (II) in an organic solvent selected from an aromatic solvent, aliphatic hydrocarbon solvent, or mixture of said solvents; said aqueous solution of sulfide or sulfhydrate, being used in an amount of from about 10 to about 50 percent in excess of that stoichiometrically required to convert said (II) to the corresponding benzotriazole N-oxide of the formula (III):

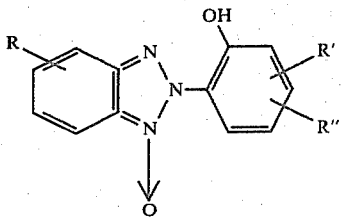

the combining occurring over a period of about 15 minutes to about 6 hours; separating the aqueous phase from the organic phase and washing the organic phase with a solution of a strong electrolyte and water to remove salts therefrom; then, in a second stage, reducing said N-oxide (III) to the benzotriazole (I) by adding water to the organic solution of (III) to form a two-phase reaction mixture at a temperature of about 50° C. to 75° C, adding thereto about 1 2 moles of zinc or tin per mole of said (III) and then adding, at a rate sufficient to maintain the reaction mixture in said temperature range, from about 1.5 to 2.5 moles per mole of (III) of an aqueous solution of an alkali metal hydroxide; then, adding sufficient strong inorganic acid to destroy excess zinc or tin and to neutralize the excess alkali metal hydroxide; filtering the insolubles therefrom; separating the organic phase from the aqueous phase and recovering said (I) from said organic phase.

2. The process of claim 1 wherein R, R' are hydrogen, R'' is para to the hydroxyl group and is tertiary octyl.

3. The process of claim 1 wherein the aqueous solution of sulfhydrate or sulfide is added to the two-phase mixture.

4. The process of claim 1 wherein the two-phase mixture is added to the aqueous solution of sulfhydrate or sulfide.

5. The process of claims 3 or 4 wherein the first stage temperature is about 50°-60° C., zinc is used at about 1.2 to 1.4 moles per mole of N-oxide, and the alkali metal hydroxide is used at about 1.7 to 2 moles per mole of N-oxide.

6. The process of claims 3 or 4 wherein the alkali metal or ammonium sulfhydrate or sulfide is sodium sulfhydrate or sodium sulfide.

7. The process of claims 3 or 4 wherein the strong electrolyte is sodium chloride.

8. The process of claim 1 wherein the organic solvent is toluene.

9. The process of claim 1 wherein the organic solvent is a mixture of paraffins and naphthenes.

10. The process of claims 1 or 2 wherein R'' is 1,1,3,3-tetramethylbutyl.

* * * * *

UNITED STATES PATENT OFFICE
CERTIFICATE OF CORRECTION

Patent No. 4,224,451          Dated September 23, 1980

Inventor(s) Rex Dana Roberts and William Baptist Hardy

It is certified that error appears in the above-identified patent and that said Letters Patent are hereby corrected as shown below:

Column 8, line 20, after "1" insert --to--

Signed and Sealed this

Thirteenth Day of January 1981

[SEAL]

Attest:

SIDNEY A. DIAMOND

Attesting Officer          Commissioner of Patents and Trademarks